US009422227B2

(12) United States Patent
Dakka et al.

(10) Patent No.: US 9,422,227 B2
(45) Date of Patent: Aug. 23, 2016

(54) SUBSTITUTED NAPHTHALENES AS FEEDSTOCK FOR PLASTICIZER PRODUCTION

(71) Applicant: ExxonMobil Research and Engineering Company, Annandale, NJ (US)

(72) Inventors: Jihad Mohammed Dakka, Whitehouse Station, NJ (US); Edmund John Mozeleski, Califon, NJ (US); Lisa Saunders Baugh, Ringoes, NJ (US); Stephen Zushma, Clinton, NJ (US)

(73) Assignee: ExxonMobil Research and Engineering Company, Annandale, NJ (US)

(*) Notice: Subject to any disclaimer, the term of this patent is extended or adjusted under 35 U.S.C. 154(b) by 469 days.

(21) Appl. No.: 13/723,553

(22) Filed: Dec. 21, 2012

(65) Prior Publication Data

US 2014/0179845 A1 Jun. 26, 2014

(51) Int. Cl.

| | |
|---|---|
| ***C07C 69/76*** | (2006.01) |
| ***C07C 69/753*** | (2006.01) |
| ***C07C 69/24*** | (2006.01) |
| ***C08K 5/10*** | (2006.01) |
| *C08K 5/00* | (2006.01) |

(52) U.S. Cl.

CPC ............... *C07C 69/76* (2013.01); *C07C 69/24* (2013.01); *C07C 69/753* (2013.01); *C08K 5/10* (2013.01); *C07C 2102/10* (2013.01); *C08K 5/0016* (2013.01)

(58) Field of Classification Search

CPC ..... C07C 69/017; C07C 69/24; C07C 69/76; C07C 69/753; C07C 67/08; C08K 5/00

See application file for complete search history.

(56) References Cited

U.S. PATENT DOCUMENTS

| | | | | |
|---|---|---|---|---|
| 1,909,092 | A | 5/1933 | Bruson | |
| 2,233,513 | A | 3/1941 | Bruson | |
| 2,372,947 | A | 4/1945 | Gresham | |
| 2,512,675 | A * | 6/1950 | Pijoan | C07C 39/17 514/729 |
| 3,110,724 | A | 11/1963 | Woodbridge et al. | |
| 3,218,277 | A * | 11/1965 | Ringwald | C08K 5/101 264/211 |
| 3,239,363 | A * | 3/1966 | Burdge | 106/316 |
| 3,255,235 | A | 6/1966 | Coran et al. | |
| 3,284,220 | A | 11/1966 | Anagnostopoulos et al. | |
| 5,095,135 | A | 3/1992 | Yamada et al. | |
| 6,740,254 | B2 | 5/2004 | Zhou et al. | |
| 7,297,738 | B2 | 11/2007 | Gosse et al. | |
| 7,919,649 | B2 | 4/2011 | Compton et al. | |
| 2002/0019559 | A1 | 2/2002 | Brunner et al. | |
| 2006/0247461 | A1 | 11/2006 | Schlosberg et al. | |

FOREIGN PATENT DOCUMENTS

| | | | |
|---|---|---|---|
| EP | 0450621 | A2 | 10/1991 |
| JP | 61-126003 | * | 6/1986 |
| WO | 9932427 | | 7/1999 |
| WO | 03029339 | A1 | 4/2003 |
| WO | 2004046078 | A1 | 6/2004 |

OTHER PUBLICATIONS

JP86 translated, 1986.*
STN Apr. 4, 1987.*
STN Jul. 19, 1986.*
STN Mar. 4, 1999.*
Zerschwitz et al. (A One-Pot Sequence of Stille and Heck Couplings: Synthesis of Various 1,3,5-Hexatrienes and Their Subsequent 6π-Electrocyclizations, Chem. Eur. J., 7, No. 18, pp. 4035-4046, 2001).*
Yamada et al. (Asymmetric Acylation of sec-Alcohols with Twisted Amides Possessing Axial Chirality Induced by the Adjacent Asymmetric Center J. Org. Chem. 1999, 64, 9365-9373).*
Cooke (Formation of Polycyclic Carbocycles through Metal- Halogen Exchange-Initiated Intramolecular Conjugate Addition Reactions, J. Org. Chem. 1993, 58, 2910-2912).*
JP86 translated (JP-61126003 1986).*
Merle-Aubry et al. (Photophysics and Photochemistry of Naphthyl Ester Polymers in Solution, Macromolecules 1980, 13, 1138-1143).*
Griebler, Christian et al., "Combined Application of Stable Carbon Isotope Analysis and Specific Metabolites Determination for Assessing in Situ Degradation of Aromatic Hydrocarbons in a Tar Oil-Contaminated Aquifer," Environmental Science and Technology, 2004, pp. 617-631, vol. 38, Issue 2.
Hunsberger, I. Moyer et al., "The Determination of Double-bond Character in Cyclic Systems. IV. Tetrahydronaphthalene. Steric Facilitation of Chelation," Journal of the American Chemical Society, 1958, pp. 3294-3300, vol. 80.
Francis, John E. et al., "Highly Selective Adenosine A2 Receptor Agonists in a Series of N-Alkylated 2- Aminoadenosines," Journal of Medicinal Chemistry, 1991, pp. 2570-2579, vol. 34, Issue 8.
Adkins, Homer et al., "Selective Hydrogenation of Esters Containing a Naphthalene Nucleus," Journal of the American Chemical Society, 1949, pp. 3528-3531, vol. 71.
Newman, Melvin S. et al., "The Catalytic Dehydrogenation of 5-Substituted 1,2,3,4-Tetrahydronaphthalene Derivatives," Journal of the American Chemical Society, 1952, pp. 905-908, vol. 74.

(Continued)

*Primary Examiner* — Yevegeny Valenrod
*Assistant Examiner* — Blaine G Doletski
(74) *Attorney, Agent, or Firm* — Robert A. Migliorini

(57) ABSTRACT

Provided are compounds and processes of making compounds of the formula:

$$R_x \text{—[naphthalene]—} R'_y,$$

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$ or —OC(O)R$_1$, wherein R$_1$ is a branched $C_4$ to $C_{14}$ alkyl, and their use in polymer compositions.

6 Claims, No Drawings

(56) References Cited

OTHER PUBLICATIONS

Markgraf, J. Hodge et al., "The Diels-Alder Reaction of Methyl Propiolate With 1-Vinylcycloalkenes," Tetrahedron Letters, 1983, pp. 241-244, vol. 24, Issue 3.
Hagishita, Sanji et al., "Optical Activity in BY-Unsaturated Ketones. Part 2. Effect of the Magnitude and Energy of the Electric Transition Dipole Moment in the Aromatic Groups in 1- and 1,5-Substituted 9,10- Ethano -9,10-dihydroanthracen-11-one Derivatives," Journal of the Chemical Society, Perkin Transactions 2: Physical Organic Chemistry, 1978, pp. 59-67, vol. 1.
Burgess, Kevin et al., "Chlorotris(triphenylphosphine)-rhodium (I)," Chem. Abstr. 2008, 149, 307083.

* cited by examiner

SUBSTITUTED NAPHTHALENES AS FEEDSTOCK FOR PLASTICIZER PRODUCTION

FIELD

This disclosure is related to a potential route to non-phthalate, aromatic OXO-ester plasticizers.

BACKGROUND

Plasticizers are incorporated into a resin (usually a plastic or elastomer) to increase the flexibility, workability, or dispensability of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for 85% worldwide of PVC plasticizer usage in 2002. However, in the recent past there has been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also co-pending, commonly-assigned, U.S. Provisional Patent Application No. 61/040,480, filed Mar. 28, 2008 and polyketones, such as described in U.S. Pat. No. 6,777,514; and also co-pending, commonly-assigned, U.S. Patent Publication No. 2008/0242895, filed Mar. 28, 2008. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers. Copending and commonly assigned U.S. Provisional Patent Application No. 61/203,626, filed Dec. 24, 2008, discloses triglycerides with a total carbon number of the triester groups between 20 and 25, produced by esterification of glycerol with a combination of acids derived from the hydroformylation and subsequent oxidation of $C_3$ to $C_9$ olefins, having excellent compatibility with a wide variety of resins and that can be made with a high throughput.

U.S. Pat. No. 3,284,220 to Anagnostopoulos et al. discloses substituted phenyl ethers of certain mono- and polycarboxylic naphthoic acids and their use as stabilizers for polymeric substances.

U.S. Pat. No. 5,095,135 to Yamada et al. discloses a process for the preparation of naphthalenecarboxylic acid esters in which a substituted naphthalene is oxidized with molecular oxygen in the presence of a heavy metal-based catalyst in a solvent comprising a lower aliphatic monocarboxylic acid to form a naphthalenecarboxylic acid and the resulting acid is then esterified. The esterified product is purified by washing, recrystallization, and distillation in that order. Heavy metals are recovered as carbonates from filtrates and washings obtained by separation of crude acid and ester products and by washing thereof.

U.S. Pat. No. 7,919,649 to Compton et al. discloses plasticizer esters produced by the catalyzed reaction of alcohols and acids or anhydrides are neutralized by treatment with an aqueous alkaline alkali metal salt solution in an amount that provides less than a stoichiometric amount of alkali metal salt in relation to the acidity of the crude ester and the amount of water present during the treatment is from 0.7 to 1.4 wt % of water based on the weight of crude ester. When using titanium as the esterification catalyst, the ester resulting from this process contains less than 0.01 ppm by weight of titanium residue, so that it is storage stable when stored in the presence of an antioxidant.

What is needed is a method of making other general purpose non-phthalate plasticizers having suitable melting or chemical and thermal stability, pour point, glass transition, increased compatibility, good performance and low temperature properties.

SUMMARY

In One Aspect, the Present Application is Directed to Compounds of the Formula:

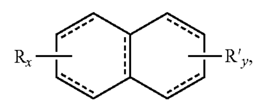

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$ or —OC(O)R$_1$, wherein R$_1$ is a branched $C_4$ to $C_{14}$ alkyl.

In preferred embodiments, the compounds are those wherein x=4, each R is H, y=4, and three of R' are H; or wherein x=8, each R is H, y=4, and three of R' are H; or those wherein x=4, each R is H, y=4, and one R' is $C_1$ to $C_4$ alkyl; or those wherein x=4, each R is H, y=8, and seven of R' are H; or those wherein x=4, each R is H, y=8, and six of R' are H and one R' is $C_1$ to $C_4$ alkyl, or those wherein x=8, at least one R is $C_1$ to $C_4$ alkyl, each remaining R is H, y=4, and three of R' are H; or those wherein x=8, and y=8.

In particularly preferred embodiments, the compounds can be those wherein R$_1$ is the hydrocarbon residue of a $C_4$ to $C_{14}$ OXO-alcohol or OXO-acid averaging from 0.2 to 4.0 branches per residue; or from 1.8 to 3.8, or from 2.0 to 3.6, or from 2.1 to 3.5 branches per residue. While the compounds can have a single ester moiety with a relatively long hydrocarbon residue, they can also have multiple ester moieties each having relatively shorter hydrocarbon residues. Advantageously, in order to obtain optimum resistance to volatility characteristics, the average number of carbons in all hydrocarbon residues should be more than 9 carbons, such as for example from 9 to 14 carbons.

For example, the compounds of the present disclosure can be represented by any of the following chemical structures:

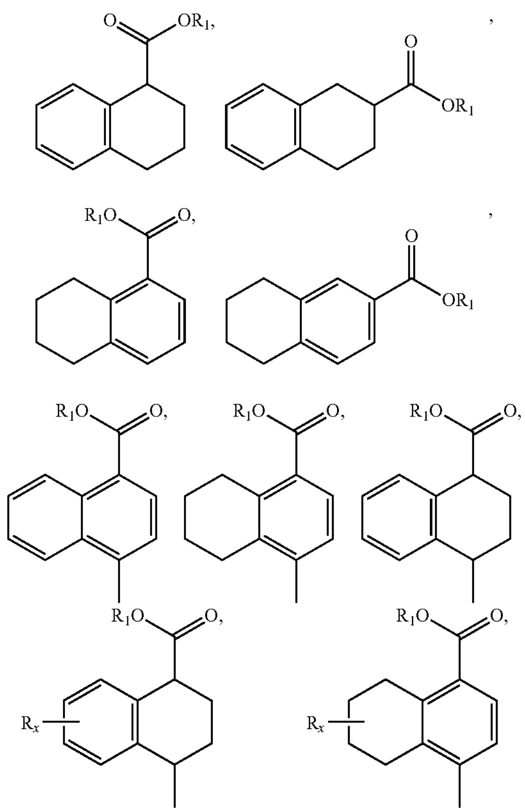

and positional isomers thereof.

In another aspect, the present application is directed to a process for making compounds of the formula:

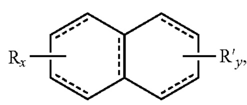

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$, wherein R$_1$ is a branched $C_4$ to $C_{14}$ alkyl, comprising: reacting optionally-alkylated naphthalene under conditions appropriate to form an optionally alkyl-substituted naphthoic acid; reacting said acid group with an OXO-alcohol under esterification conditions to form naphthoic acid esters; and optionally hydrogenating said naphthoic acid esters.

For example, when hydrogenating is conducted a tetrahydro naphthoic acid ester is formed, which can be a tetrahydro-1-naphthoic acid ester, or a tetrahydro-2-naphthoic acid ester.

In a further embodiment, the present application is directed to a process for making compounds of the formula:

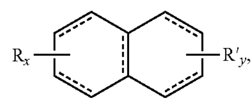

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$, wherein R$_1$ is a branched $C_4$ to $C_{14}$ alkyl, comprising: selectively hydrogenating an optionally-alkylated naphthalene to form an optionally-alkylated dihydronaphthalene; hydroformylating the optionally-alkylated dihydronaphthalene to form a corresponding aldehyde; oxidizing the aldehyde to form a corresponding acid; and esterifying the acid.

In an alternative embodiment, the present application is directed to a process for making compounds of the formula:

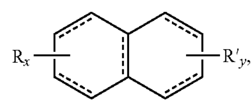

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —OC(O)R$_1$, wherein R$_1$ is a branched $C_4$ to $C_{14}$ alkyl, comprising: hydroxylation of an optionally-alkylated naphthalene with hydroperoxide to form an optionally-alkylated naphthol, or hydration of an optionally-alkylated dihydronaphthalene to form an optionally-alkylated tetrahydronaphthalenol, or oxidative decarboxylation of an optionally-alkylated naphthoic acid to form an optionally-alkylated naphthol; esterifying the optionally-alkylated naphthol or optionally-alkylated tetrahydronaphthalenol with $C_4$ to $C_{14}$ alkanoic acid; and optionally hydrogenating said optionally-alkylated naphthol.

Additionally, the present application is directed to a polymer composition comprising a thermoplastic polymer and at least one plasticizer of the formula:

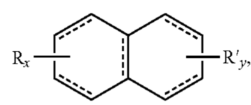

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —CO$_2$R$_1$ or —OC(O)R$_1$, wherein R$_1$ is a branched $C_4$ to $C_{14}$ alkyl, in which the thermoplastic polymer can be selected from the group consisting of vinyl chloride resins, polyesters, polyurethanes, ethylene-vinyl acetate copolymer, rubbers, poly(meth)acrylics and combinations thereof.

DETAILED DESCRIPTION

All numerical values within the detailed description and the claims herein are modified by "about" or "approximately" the indicated value, and take into account experimental error and variations that would be expected by a person having ordinary skill in the art.

There is an increased interest in developing new plasticizers that are non-phthalates and which possess good plasticizer performance characteristics but are still competitive economically. The present disclosure is directed towards non-phthalate ester plasticizers, particularly OXO-ester plasticizers, that can be made from low cost feeds and employ fewer manufacturing steps in order to meet economic targets.

It has been determined that compounds of the general formula

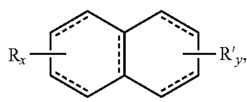

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$ or —OC(O)R$_1$, wherein R$_1$ is a branched $C_4$ to $C_{14}$ alkyl, are particularly useful as replacements for diisononylphthalate (DINP) as plasticizers for conventional polymer plastics.

One route to non-phthalate plasticizers of the present disclosure is by catalyzed oxidation of a mono- or dialkyl naphthalene to form a naphthoic acid, as follows:

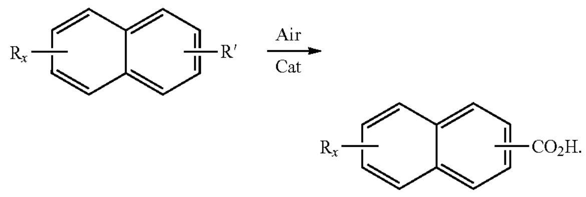

Subsequently, the naphthoic acid can be esterified by reaction with an alcohol:

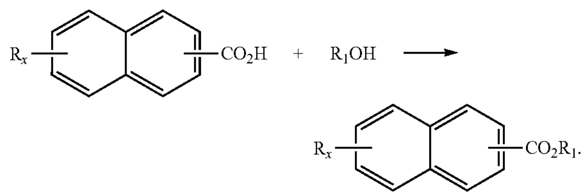

The naphthoic acid esters so-formed find use as plasticizers according to the present disclosure. Optionally, the naphthoic acid esters can be further modified by hydrogenation of one or both aromatic rings to form either optionally alkylated tetrahydronaphthoic acid esters or optionally alkylated dicyclohexyl esters, as follows:

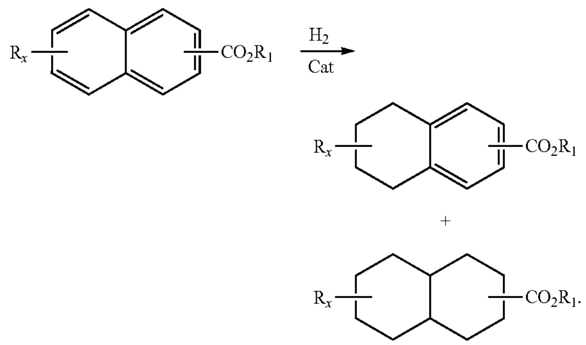

The melting characteristics, chemical stability, thermal stability, pour point, glass transition, polymer compatibility, plasticizer performance and low temperature properties of the above-disclosed esters can be modified by varying the number of carbons in the alkyl chains R and R$_1$.

Another route to non-phthalate plasticizers of the present disclosure is by selective hydrogenation of an optionally-substituted naphthalene to form a dihydronaphthalene, followed by hydroformylation to form aldehyde-substituted compounds as follows:

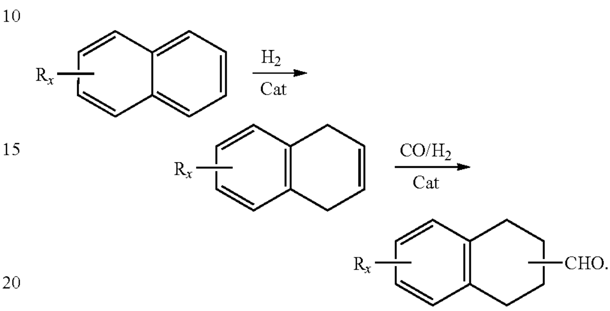

Subsequently, the aldehyde substituent is oxidized to form the corresponding naphthoic acid, and the acid group is esterified with a suitable alcohol, as illustrated below:

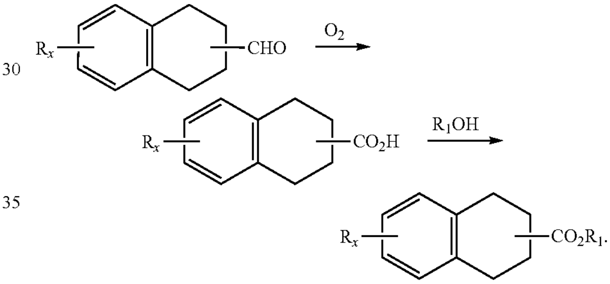

In more preferred embodiments, the resulting optionally-alkylated naphthoic acids are esterified with OXO-alcohols, which are mixed linear and branched alcohol isomers, the formation of which is described in more detail below.

An "OXO-alcohol" is an organic alcohol, or mixtures of organic alcohols, which is prepared by hydroformylating an olefin, followed by hydrogenation to form the alcohols. An "OXO-acid" is an organic acid, or mixture of organic acids, which is prepared by hydroformylating an olefin, followed by oxidation to form the acids. Typically, the olefin is formed by light olefin oligomerization over heterogenous acid catalysts, which olefins are readily available from refinery processing operations. The reaction results in mixtures of longer-chain, branched olefins, which subsequently form longer chain, branched alcohols or acids, as described in U.S. Pat. No. 6,274,756, incorporated herein by reference in its entirety. The OXO-alcohols consist of multiple isomers of a given chain length due to the various isomeric olefins obtained in the oligomerization process, in tandem with the multiple isomeric possibilities of the hydroformylation step. The OXO-acids similarly consist of multiple isomers of a given chain length.

An "OXO-ester" is a compound having at least one functional ester moiety within its structure derived from esterification of either an acid or alcohol compound with an OXO-alcohol or OXO-acid, respectively.

"Hydroformylating" or "hydroformylation" is the process of reacting a compound having at least one carbon-carbon double bond (an olefin) in an atmosphere of carbon monoxide and hydrogen over a cobalt or rhodium catalyst, which results in addition of at least one aldehyde moiety to the underlying compound. U.S. Pat. No. 6,482,972, which is incorporated herein by reference in its entirety, describes the hydroformylation (OXO) process.

Branched aldehydes can be produced by hydroformylation of $C_3$ to $C_{12}$ olefins; in turn, some of these olefins have been produced by propylene and/or butene oligomerization over solid phosphoric acid or zeolite catalysts. The resulting $C_4$ to $C_{14}$ aldehydes can then be recovered from the crude hydroformylation product stream by fractionation to remove unreacted olefins. These $C_4$ to $C_{13}$ aldehydes can then hydrogenated to alcohols (OXO-alcohols) or oxidized to acids (OXO-acids). Single carbon number acids or alcohols can be used in the esterification of the aromatic acids described above, or differing carbon numbers can be used to optimize product cost and performance requirements. The "OXO" technology provides cost advantaged alcohols and acids. Other options are considered, such as hydroformylation of $C_4$-olefins to $C_5$-aldehydes, followed by hydrogenation to $C_5$-alcohols, or aldehyde dimerization followed by hydrogenation or oxidation to $C_{10}$ alcohols or acids. It is understood that the term "branched" describes the overall isomeric mixture of the aldehydes (and subsequent acids, alcohols, and $R_1$ residues). Thus, a "branched" OXO-aldehyde, acid, alcohol, or residue contains some portion of linear isomers mixed in with the individual branched isomers.

"Hydrogenating" or "hydrogenation" is addition of hydrogen ($H_2$) to a double-bonded functional site of a molecule, such as in the present case the addition of hydrogen to the aldehyde to form the corresponding alcohol, and saturation of the double bonds in an aromatic ring. Conditions for hydrogenation of an aldehyde are well-known in the art and include, but are not limited to temperatures of 0-300° C., pressures of 1-500 atmospheres, and the presence of homogeneous or heterogeneous hydrogenation catalysts such as Pt/C, $Pt/Al_2O_3$ or $Pd/Al_2O_3$.

Alternatively, the OXO-acids or OXO-alcohols can be prepared by aldol condensation of shorter-chain aldehydes to form longer chain aldehydes, as described in U.S. Pat. No. 6,274,756, followed by oxidation or hydrogenation to form the OXO-acids or OXO-alcohols, respectively.

"Esterifying" or "esterification" is reaction of a carboxylic acid moiety, such as an anhydride, with an organic alcohol moiety to form an ester linkage. Esterification conditions are well-known in the art and include, but are not limited to, temperatures of 0-300° C. and the presence or absence of homogeneous or heterogeneous esterification catalysts such as Lewis or Brønsted acid catalysts.

As discussed above, the resulting OXO-alcohols and OXO-acids can be used individually or together in mixtures having different chain lengths, or in isomeric mixtures of the same carbon chain length to make mixed esters for use as plasticizers. This mixing of carbon numbers and/or levels of branching can be advantageous to achieve the desired compatibility with PVC for the respective core alcohol or acid used for the polar moiety end of the plasticizer, and to meet other plasticizer performance properties. The preferred OXO-alcohols or OXO-acids are those having from 4 to 14 carbons, more preferably $C_5$ to $C_{13}$ alcohols/acids, and even more preferably $C_9$ to $C_{13}$ alcohols/acids, depending on the number of ester moieties and the desired volatility of the compound.

The overall isomeric distribution of the OXO-acids or OXO-alcohols may be described quantitatively by parameters such as average branch content per molecule or per chain position. Branching, may be determined by Nuclear Magnetic Resonance (NMR) spectroscopy.

In one embodiment the preferred OXO-alcohols are those which result in $R_1$ being a hydrocarbon residue of a $C_4$ to $C_{14}$ OXO-alcohol averaging from 0.2 to 4.0 branches per residue, or from 1.8 to 3.8, or from 2.0 to 3.6, or from 2.1 to 3.5 branches per residue.

Typical branching characteristics of OXO-alcohols are provided in Table 1, below.

TABLE 1

$^{13}C$ NMR Branching Characteristics of Typical OXO-Alcohols.

| OXO-Alcohol | Avg. Carbon No. | % of α-Carbons w/Branches[a] | β-Branches per Molecule[b] | Total Methyls per Molecule[c] | Pendant Methyls per Molecule[d] | Pendant Ethyls per Molecule |
|---|---|---|---|---|---|---|
| $C_4$[e] | 4.0 | 0 | 0.35 | 1.35 | 0.35 | 0 |
| $C_5$[f] | 5.0 | 0 | 0.30 | 1.35 | 0.35 | 0 |
| $C_6$ | — | — | — | — | — | — |
| $C_7$ | 7.3 | 0 | 0.15 | 1.96 | 0.99 | 0.04 |
| $C_8$ | 8.6 | 0 | 0.09 | 3.0 | 1.5 | — |
| $C_9$ | 9.66 | 0 | 0.09 | 3.4 | — | — |
| $C_{10}$ | 10.2 | 0 | 0.16 | 3.2 | — | — |
| $C_{12}$ | 12.2 | 0 | — | 4.8 | — | — |
| $C_{13}$ | 13.1 | 0 | — | 4.4 | — | — |

— Data not available.

[a]—COH carbon.

[b]Branches at the —$CCH_2OH$ carbon.

[c]This value counts all methyl groups, including $C_1$ branches, chain end methyls, and methyl endgroups on $C_2$+ branches.

[d]$C_1$ branches only.

[e]Calculated values based on an assumed molar isomeric distribution of 65% n-butanol and 35% isobutanol (2-methylpentanol).

[f]Calculated values based on an assumed molar isomeric distribution of 65% n-pentanol, 30% 2-methylbutanol, and 5% 3-methylbutanol.

In one embodiment, the present disclosure is directed to compounds of the formula:

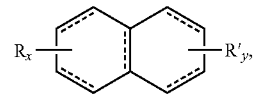

wherein x=4 to R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$ or —OC(O)R$_1$, wherein R$_1$ is a branched $C_4$ to $C_{14}$ alkyl.

The rings can have various levels of hydrogenation. Accordingly, in one embodiment wherein no hydrogenation has been conducted, both rings of the compounds are unsaturated, such as where x=4 and y=4, in which case each R is hydrogen and three of R' are hydrogen and one R' represents a single ester moiety replacing one ring hydrogen. In another embodiment, x=8, R═H, and y=4, in which case the compound is an OXO-ester of 5,6,7,8-tetrahydro naphthalene. Alternatively, the ring having the ester moiety can be the hydrogenated ring, such that x=4, with each R being hydrogen, and y=8, with seven of R' being hydrogen.

In another embodiment, either ring can be alkylated, in which case one or more R or R' is a $C_1$ to $C_4$ alkyl. In a preferred embodiment, x=4, with each R being hydrogen, and y=4, with two of R' being hydrogen, one R' being $C_1$ to $C_4$ alkyl, another R' being the ester moiety. In a more preferred embodiment one R' is methyl.

Accordingly, the preferred compounds can be represented by any one of the following structures:

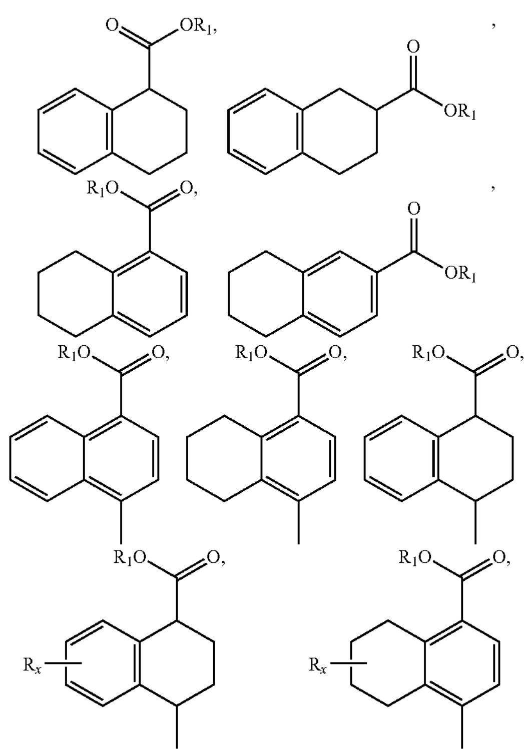

and positional isomers thereof.

In another embodiment the disclosure is directed to a process for making compounds of the formula:

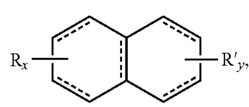

wherein x=4 to 8, R is H, $C_1$ to $C_4$ alkyl, —C(O)OR$_1$ or —OC(O)R$_1$, y=4 to 8, R" is H, $C_1$ to $C_4$ alkyl, and at least one R' is —C(O)OR$_1$, wherein R$_1$ is a branched $C_4$ to $C_{14}$ alkyl, comprising:

reacting an optionally-alkylated naphthalene under conditions appropriate to form an optionally alkyl-substituted naphthoic acid;

reacting said acid group with an OXO-alcohol under esterification conditions to form optionally-alkylated naphthoic acid esters; and optionally hydrogenating said optionally-alkylated naphthoic acid esters.

According to this embodiment, the hydrogenating step results in forming a tetrahydro naphthoic acid ester, such as either a tetrahydro-1-naphthoic acid ester, or a tetrahydro-2-naphthoic acid ester.

In another embodiment, the disclosure is directed to a process for making compounds of the formula:

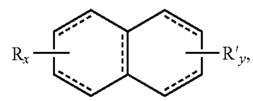

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$, wherein R$_1$ is a branched $C_4$ to $C_{14}$ alkyl, comprising:

selectively hydrogenating an optionally-alkylated naphthalene to form an optionally-alkylated dihydronaphthalene;

hydroformylating the optionally-alkylated dihydronaphthalene to form a corresponding aldehyde;

oxidizing the aldehyde to form a corresponding acid; and esterifying the acid.

In another embodiment the disclosure is directed to a process for making compounds of the formula:

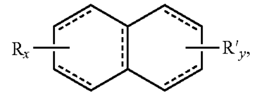

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —OC(O)R$_1$, wherein R$_1$ is a branched $C_4$ to $C_{14}$ alkyl, comprising:

hydroxylation of an optionally-alkylated naphthalene with hydroperoxide to form an optionally-alkylated naphthol, or hydration of an optionally-alkylated dihydronaphthalene to form an optionally-alkylated tetrahydronaphthalenol, or oxidative decarboxylation of an optionally-alkylated naphthoic acid to form an optionally-alkylated naphthol;

esterifying the optionally-alkylated naphthol or optionally-alkylated tetrahydronaphthalenol with $C_4$ to $C_{14}$ alkanoic acid; and optionally hydrogenating said optionally-alkylated naphthol.

According to this process, an optionally-substituted naphthol, such as 5,6,7,8-tetrahydro-2-naphthol, can be formed or used as the starting material, and the alcohol moiety is esterified with a suitable carboxylic acid:

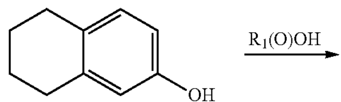

-continued

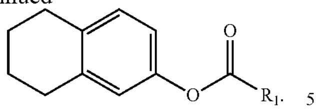

In this case, the suitable carboxylic acids can be selected to optimize the characteristics of the resulting esters for use as plasticizers. For example, suitable carboxylic acids are branched carboxylic acids having from 4 to 14 carbons, such as OXO-acids.

According to this embodiment, the preferred OXO-acids are those which result in $R_1$ being a hydrocarbon residue of a $C_4$ to $C_{14}$ OXO-alcohol averaging from 0.2 to 4.0 branches per residue; or from 1.8 to 3.8, or from 2.0 to 3.6, or from 2.1 to 3.5 branches per residue.

Typical branching characteristics of OXO-acids are provided in Table 2, below.

TABLE 2

$^{13}C$ NMR Branching Characteristics of Typical OXO-Acids.

| OXO-Acid | Average Carbon No. | Pendant Methyls[a] | Total Methyls[b] | Pendant Ethyls | % Carbonyls α to Branch[c] |
|---|---|---|---|---|---|
| $C_4$[d] | 4.0 | 0.35 | 1.35 | 0 | 35 |
| $C_5$[e] | 50 | 0.35 | 1.35 | 0 | 30 |
| $C_6$ | — | — | — | — | — |
| $C_7$ | 6.88-7.92 | 0.98-1.27 | 1.94-2.48 | 0.16-0.26 | 11.3-16.4 |
| $C_8$ | 8.1-8.3 | — | 2.7 | — | 12-15 |
| $C_9$ | 9.4 | — | n/a | — | 12 |
| $C_{10}$ | 10.2 | — | n/a | — | 12 |
| $C_{12}$ | — | — | — | — | — |
| $C_{13}$ | 12.5 | — | 4.4 | — | 11 |

—Data not available.

[a]$C_1$Branches only.

[b]Includes methyls on all branch lengths and chain end methyls.

[c]The "alpha" position in the acid nomenclature used here is equivalent to the alcohol "beta" carbon in Table 1.

[d]Calculated values based on an assumed molar isomeric distribution of 65% n-butanoic acid and 35% isobutanoic acid (2-methylpentanoic acid).

[e]Calculated values based on an assumed molar isomeric distribution of 65% n-pentanoic acid, 30% 2-methylbutanoic acid, and 5% 3-methylbutanoic acid.

In general, for every polymer to be plasticized, a plasticizer is required with the correct balance of solubility, volatility and viscosity to have acceptable plasticizer compatibility with the resin. In particular, if the 20 C. kinematic viscosity is higher than 250 $mm^2$/sec as measured by the appropriate ASTM test, or alternately if the 20° C. cone-and-plate viscosity is higher than 250 cP, this will affect the plasticizer processability during formulation, and can require heating the plasticizer to ensure good transfer during storage and mixing of the polymer and the plasticizer. Volatility is also a very critical factor which affects the long-term plasticizer formulation stability. Higher volatility plasticizers can migrate from the plastic resin matrix and cause damage to the article. The plasticizer volatility in a resin matrix can be roughly predicted by neat plasticizer weight loss at 220° C., using Thermogravimetric Analysis.

We have found that when $C_4$ to $C_{14}$ OXO-alcohols and acids are used as reactants for the esterification reactions described above, the resulting OXO-esters are in the form of relatively high-boiling liquids (having low volatility), which are readily incorporated into polymer formulations as plasticizers.

Accordingly, another embodiment of this disclosure is directed to a polymer composition comprising a thermoplastic polymer and at least one plasticizer of the formula:

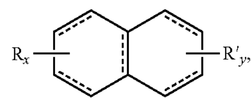

wherein x=4 to 8, R is H, $C_1$ to $C_4$ alkyl, —C(O)O$R_1$ or —OC(O)$R_1$, y=4 to 8, R' is H, $C_1$ to $C_4$ alkyl, and at least one R' is —$CO_2R_1$ or —OC(O)$R_1$, wherein $R_1$ is a branched $C_4$ to $C_{14}$ alkyl. These new plasticizer compounds can be added to thermoplastic polymers, such as vinyl chloride resins, polyesters, polyurethanes, ethylene-vinyl acetate copolymer, rubbers, poly(meth)acrylics and combinations thereof, preferably polyvinylchloride.

Thus, in one aspect, the present application is directed to compounds of the formula:

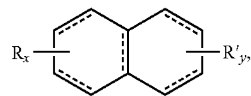

wherein x=4 to 8, R is H, $C_1$ to $C_4$ alkyl, —C(O)O$R_1$ or —OC(O)$R_1$, y=4 to 8, R' is H, $C_1$ to $C_4$ alkyl, and at least one R' is —C(O)O$R_1$ or —OC(O)$R_1$ wherein $R_1$ is a branched $C_4$ to $C_{14}$ alkyl.

In preferred embodiments, the compounds are those wherein x=4, each R is H, y=4, and three of R' are H; or wherein x=8, each R is H, y=4, and three of R' are H; or those wherein x=4, each R is H, y=4, and one R' is $C_1$ to $C_4$ alkyl; or those wherein x=4, each R is H, y=8, and seven of R' are H; or those wherein x=4, each R is H, y=8, and six of R' are H and one R' is $C_1$ to $C_4$ alkyl, or those wherein x=8, at least one R is $C_1$ to $C_4$ alkyl, each remaining R is H, y=4, and three of R' are H; or those wherein x=8, and y=8.

In particularly preferred embodiments, the compounds are those in which $R_1$ is a hydrocarbon residue of a $C_4$ to $C_{14}$ OXO-alcohol averaging from 0.2 to 4.0 branches per residue; or from 1.8 to 3.8, or from 2.0 to 3.6, or from 2.1 to 3.5 branches per residue.

For example, the compounds of the present disclosure can be represented by any of the following chemical structures:

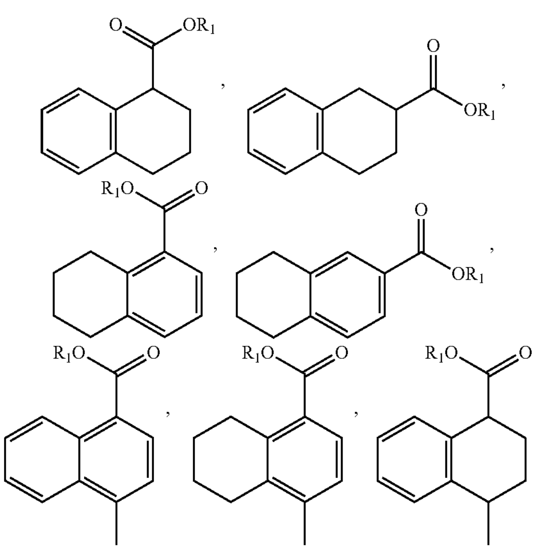

-continued

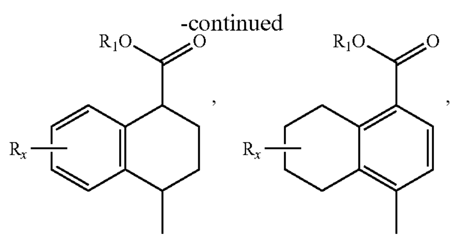

and positional isomers thereof.

In another aspect, the present application is directed to a process for making compounds of the formula:

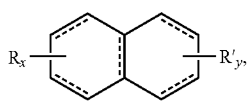

wherein x=4 to 8, R is H, $C_1$ to $C_4$ alkyl, —C(O)OR$_1$ or —OC(O)R$_1$, y=4 to 8, R' is H, $C_1$ to $C_4$ alkyl, and at least one R' is —C(O)OR$_1$, wherein R$_1$ is a branched $C_4$ to $C_{14}$ alkyl, comprising: reacting alkylated naphthalene under conditions appropriate to form an optionally alkyl-substituted naphthoic acid; reacting said acid group with an OXO-alcohol under esterification conditions to form naphthoic acid esters; and optionally hydrogenating said naphthoic acid esters into a tetrahydro naphthoic acid ester, which can be either a tetrahydro-1-naphthoic acid ester, or a tetrahydro-2-naphthoic acid ester, or a mixture thereof.

In an alternative embodiment, the process can include selectively hydrogenating the optionally-alkylated naphthalene to form an optionally-alkylated dihydronaphthalene; hydroformylating the optionally-alkylated dihydronaphthalene to form a corresponding aldehyde; oxidizing the aldehyde to form a corresponding acid; and esterifying the acid.

In another alternative embodiment, the process can comprise hydroxylation of an optionally-alkylated naphthalene with hydroperoxide to form an optionally-alkylated naphthol, or hydration of an optionally-alkylated dihydronaphthalene to form an optionally-alkylated tetrahydronaphthalenol, or oxidative decarboxylation of an optionally-alkylated naphthoic acid to form an optionally-alkylated naphthol; esterifying the optionally-alkylated naphthol or optionally-alkylated tetrahydronaphthalenol with $C_4$ to $C_{14}$ alkanoic acid; and optionally hydrogenating said optionally-alkylated naphthol.

Additionally, the present application is directed to a polymer composition comprising a thermoplastic polymer and at least one plasticizer of the formula:

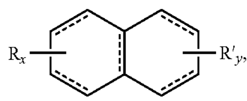

wherein x=4 to 8, R is H, $C_1$ to $C_4$ alkyl, —C(O)OR or —OC(O)R$_1$, y=4 to 8, R' is H, $C_1$ to $C_4$ alkyl, and at least one R' is —CO$_2$R$_1$ or —OC(O)R$_1$, wherein R$_1$ is a branched $C_4$ to $C_{14}$ alkyl, in which the thermoplastic polymer can be selected from the group consisting of vinyl chloride resins, polyesters, polyurethanes, ethylene-vinyl acetate copolymer, rubbers, poly(meth)acrylics and combinations thereof.

The following examples are meant to illustrate the present disclosure and inventive processes, and provide where appropriate, a comparison with other methods, including the products produced thereby. Numerous modifications and variations are possible and it is to be understood that within the scope of the appended claims, the disclosure can be practiced otherwise than as specifically described herein.

EXAMPLES

Example 1

Esterification of 1,2,3,4-Tetrahydro-1-Napthoic Acid with OXO—$C_9$ Alcohols

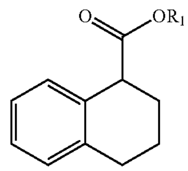

Into a 4-necked 500 ml round bottom flask equipped with an air stirrer, nitrogen inductor, chilled water cooled condenser, Dean-Stark trap and an out bubbler were added 1,2,3,4-tetrahydro-1-napthoic acid (49.02 g, 0.2782 mole), OXO—$C_9$ alcohols (120.51 g, 0.8345 moles) and xylenes (86.4 g, 0.814 mole). The reaction mixture was heated at 160-220° C. with air stirring under nitrogen for 17 hours. The excess alcohols and xylenes were removed under vacuum to 0.10 mm. The crude residual product was a clear orange liquid, with a purity of 99.65% by GC analysis.

Example 2

Esterification of 5,6,7,8-Tetrahydro-1-Napthalene Carboxylic Acid with OXO—$C_9$ Alcohols

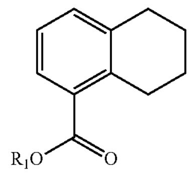

Into a 4-necked 500 ml round bottom flask equipped with an air stirrer, nitrogen inductor, chilled water cooled condenser, Dean-Stark trap and an out bubbler were added 5,6,7,8-tetrahydro-1-napthalene carboxylic acid (48.90 g, 0.2775 mole), OXO—$C_9$ alcohols (120.2 g, 0.8325 moles) and xylenes (75.1 g, 0.707 mole). The reaction mixture was heated at 163-210° C. with air stirring under nitrogen for 14 hours. The excess alcohols and xylenes were removed under vacuum to 0.10 mm. The crude residual product was treated with charcoal at room temperature with stirring for 2 hours. The mixture was filtered twice to remove the charcoal, a clear & colorless liquid resulted with a purity of 99.7% by GC analysis.

Example 3

Esterification of 5,6,7,8-Tetrahydro-1-Napthalene Carboxylic Acid with Oxo-$C_{10}$ Alcohols

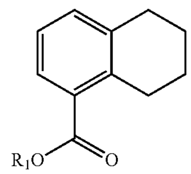

Into a 4-necked 500 ml round bottom flask equipped with an air stirrer, nitrogen inductor, chilled water cooled condenser, Dean-Stark trap and an out bubbler were added 5,6,7,8-tetrahydro-1-napthalene carboxylic acid (52.0 g, 0.2951 mole), OXO—$C_{10}$ alcohols (140.2 g, 0.8853 moles) and xylenes (52 g, 0.4896 mole). The reaction mixture was heated at 187-215° C. with air stirring under nitrogen for 15 hours. The excess alcohols and xylenes were removed under vacuum to 0.10 ram. The crude residual product was treated with charcoal at room temperature with stirring for 2 hours. The mixture was filtered twice to remove the charcoal, a clear & colorless liquid resulted with a purity of 99.4% by GC analysis.

Example 4

Esterification of 5,6,7,8-Tetrahydro-2-Napthol with OXO—$C_{10}$ Acids

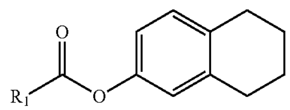

Into a 4-necked 500 ml round bottom flask equipped with an air stirrer, nitrogen inductor, chilled water cooled condenser, Dean-Stark trap and an out bubbler were added 5,6,7,8-tetrahydro-2-napthol (50.0 g, 0.34 mole), OXO—$C_{10}$ acids (174.34 g, 1.012 moles) and toluene (59.6 g, 0.647 mole). The reaction mixture was heated at 129-222° C. with air stirring under nitrogen for 24 hours. The excess acids and toluene were removed under vacuum to 0.10 mm. The product was distilled overhead, bp=180° C./0.10 mm. The distillate was a clear yellow liquid with a purity of 99.2% by CC analysis.

Example 5

Esterification of 5,6,7,8-Tetrahydro-2-Napthoic Acid with Oxo-$C_{10}$ Alcohols

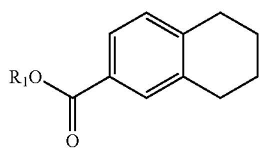

Into a 4-necked 500 ml round bottom flask equipped with an air stirrer, nitrogen inductor, chilled water cooled condenser, Dean-Stark trap and an out bubbler were added 5,6,7,8-tetrahydro-2-napthoic acid (50.2 g, 0.2849 mole), OXO—$C_{10}$ alcohols (135.35 g, 0.8345 moles) and toluene (73.0 g, 0.792 mole). The reaction mixture was heated at 142-220° C. with air stirring under nitrogen for 17 hours. The excess alcohols and xylenes were removed under vacuum to 0.10 mm. The crude residual product was filtered, a clear very light yellow liquid resulted, with a purity of 99.6% by GC analysis.

Example 6

Esterification of 5,6,7,8-Tetrahydro-1-Napthalene Carboxylic Acid with Oxo-$C_{13}$ Alcohols

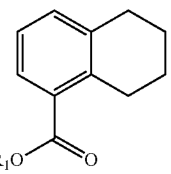

Into a 4-necked 500 ml round bottom flask equipped with an air stirrer, nitrogen inductor, chilled water cooled condenser, Dean-Stark trap and an out bubbler were added 5,6,7,8-tetrahydro-1-napthalene carboxylic acid (50.02 g, 0.2839 mole), OXO—$C_{13}$ alcohols (170.65 g, 0.8516 moles) and toluene (65 g, 0.7065 mole). The reaction mixture was heated at 148-220° C. with air stirring under nitrogen for 25 hours. The excess alcohols and toluene were removed under vacuum to 0.10 mm. The crude residual product was a clear yellow liquid, with a purity of 97.5% by GC analysis.

Example 7

Esterification of 5,6,7,8-Tetrahydro-2-Napthoic with OXO—$C_{13}$ Alcohols

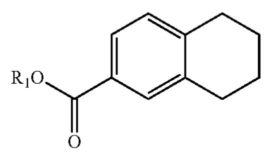

Into a 4-necked 500 ml round bottom flask equipped with an air stirrer, nitrogen inductor, chilled water cooled condenser, Dean-Stark trap and an out bubbler were added 5,6,7,8-tetrahydro-2-napthoic acid (101.5 g, 0.5764 mole), OXO—$C_{13}$ alcohols (346.5 g, 1.7292 moles) and xylenes (55.6 g, 0.5235 mole). The reaction mixture was heated at 220° C. with air stirring under nitrogen for 13 hours. The excess alcohols and xylenes were removed under vacuum to 0.10 mm. The crude residual product was filtered, a clear light yellow liquid resulted, with a purity of 98.5% by GC analysis.

Example 8

Esterification of 4-Methyl-1-Napthoic Acid with OXO—$C_{10}$ Alcohols

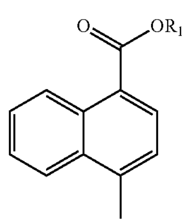

Into a 4-necked 500 ml round bottom flask equipped with an air stirrer, nitrogen inductor, chilled water cooled condenser, Dean-Stark trap and an out bubbler were added 4-methyl-1-napthoic acid (50.0 g, 0.27 mole), OXO—$C_{10}$ alcohols (127.6 g, 0.81 moles) and xylenes (53.0 g, 0.50 mole). The reaction mixture was heated at 180-224° C. with air stirring under nitrogen for 19 hours. The excess alcohols and xylenes were removed under vacuum to 0.10 mm. The crude residual product was treated with charcoal at room temperature with stirring for 2 hours. The mixture was filtered twice to remove the charcoal, a clear brown liquid resulted with a purity of 99.5% by GC analysis.

Example 9

Differential Scanning Calorimetry (DSC) and Thermogravimetric Analysis (TGA) Property Study of Esters Thermogravimetric Analysis (TGA) was conducted on the neat esters using a TA Instruments TGA5000 instrument (25-450° C., 10° C./min, under 25 cc $N_2$/min flow through furnace and 10 cc $N_2$/min flow through balance; sample size approximately 10 mg). Table 3 provides comparisons of volatilities and glass transitions (Tgs) of the different ester fractions. Tgs given in Table 3 are midpoints of the DSC second heats (unless only one heat cycle was performed, in which case the first heat Tg, which is typically in very' close agreement, is given). Differential Scanning calorimetry (DSC) was performed using a TA Instruments Q2000 calorimeter fitted with a liquid $N_2$ cooling accessory. Samples were loaded at room temperature and cooled to −130° C. at 10° C./min and analyzed on heating to 75° C. at a rate of 10° C./min. Viscosity measurements were performed on an Anton-Paar cone-and-plate viscometer using a 0.1 mL sample size. Results are summarized in Table 3. Comparative data for a common commercial plasticizer (diisononyl phthalate; Jayflex® DINP, ExxonMobil Chemical Co.) is also included.

TABLE 3

Volatility, Viscosity, and Glass Transition Properties of Neat Esters.

| Ex. No. | TGA 1% Wt Loss (° C.) | TGA 5% Wt Loss (° C.) | TGA 10% Wt Loss (° C.) | TGA Wt Loss at 220° C. (%) | DSC $T_g$ (° C.) | Viscosity (20° C., cP) |
|---|---|---|---|---|---|---|
| DINP | 184.6 | 215.2 | 228.5 | 6.4 | −79.1 | 99.2 |
| 1 | 132.0 | 163.5 | 179.4 | 48.9 | −85.6 | 31.58 |
| 2 | 137.2 | 173.8 | 190.7 | 30.7 | −81.1 | 40.55 |
| 3 | 144.2 | 179.8 | 196.9 | 24.5 | −81.1 | 45.42 |
| 4 | 145.1 | 175.5 | 190.7 | 32.6 | −78.7 | 51.16 |
| 5 | 160.5 | 191.4 | 206.7 | 17.3 | −78.5 | 75.9 |
| 6 | 167.2 | 201.4 | 217.9 | 10.8 | −74.3 | 95.09 |
| 7 | 169.9 | 207.1 | 223.3 | 8.6 | −71.7 | 193.57 |
| 8 | 171.5 | 203.6 | 219.7 | 10.1 | −69.6 | 94.80 |

— = Data not taken.

General Procedure for the Use of Esters to Plasticize Poly (Vinyl Chloride)

A 4.5 g portion of the ester sample was weighed into an Erlenmeyer flask which had previously been rinsed with uninhibited tetrahydrofuran (THF) to remove dust. A 0.63 g portion of a 70:30 by weight solid mixture of powdered Drapex® 6.8 (Crompton Corp.) and Mark® 4716 (Chemtura USA Corp.) stabilizers were added along with a stirbar. The solids were dissolved in 90 mL uninhibited THF. Oxy Vinyls® 240F PVC (9.0 g) was added in powdered form and the contents of the flask were stirred overnight at room temperature until dissolution of the PVC was complete (a PVC solution for preparation of an unplasticized comparative sample was prepared using an identical amount of stabilizer, 100 mL solvent, and 13.5 g PVC). The clear solution was poured evenly into a flat aluminum paint can lid (previously rinsed with inhibitor-free THF to remove dust) of dimensions 7.5" diameter and 0.5" depth. The lid was placed into an oven at 60° C. for 2 hours with a moderate nitrogen purge. The pan was removed from the oven and allowed to cool for a 5 min period. The resultant clear film was carefully peeled off of the aluminum, flipped over, and placed back evenly into the pan. The pan was then placed in a vacuum oven at 70° C. overnight to remove residual THF. The dry, flexible, almost colorless film was carefully peeled away and exhibited no oiliness or inhomogeneity. The film was cut into small pieces to be used for preparation of test bars by compression molding (size of pieces was similar to the hole dimensions of the mold plate). The film pieces were stacked into the holes of a multi-hole steel mold plate, pre heated to 170° C., having hole dimensions 20 mm×12.8 mm×1.8 mm (ASTM D1693-95 dimensions). The mold plate was pressed in a PHI Company QL-433-6-M2 model hydraulic press equipped with separate heating and cooling platforms. The upper and lower press plates were covered in Teflon™-coated aluminum foil and the following multistage press procedure was used at 170° C. with no release between stages: (1) 3 minutes with 1-2 ton overpressure; (2) 1 minute at 10 tons; (3) 1 minute at 20 tons; (4) 1 minute at 30 tons; (5) 3 additional minutes at 30 tons; (6) release and 3 minutes in the cooling stage of the press (7° C.) at 30 tons. A knockout tool was then used to remove the sample bars with minimal flexion.

Example 10

Properties of PVC Bars Plasticized with Esters Versus PVC Bars Plasticized with Commercial Plasticizer PVC test bars containing 50 phr of the esters of Examples 1-8 were prepared as described above. Two each of the sample bars were visually evaluated for flexibility, appearance, and clarity by placing the bars over a standard printed text. The qualitative and relative flexibility of the bars was also crudely evaluated by hand. The various bars were evaluated in different test batches; thus, a new DINP control bar was included with each batch. The bars were allowed to sit under ambient conditions at room temperature for at least three weeks and re-evaluated. Table 4 presents results.

TABLE 4

Initial and Room Temperature Aging Clarity and Appearance Properties of Ester-Containing PVC Bars and DINP-Containing PVC Control Bars.

| Example No. (Plasticizer Used in Bar) | Initial Clarity Value*,[a] | Final Clarity Value (Day 27) | Notes on Bar |
|---|---|---|---|
| 1 | 1 | 1 | OK flex~DINP |
| 2 | 1 | 1 | OK flex/moderately stiff (flex < DINP) |
| 3 | 1 | 1 | OK flex/moderately stiff (flex < DINP) |
| 4 | 1 | 1 | OK/good flex, sl. > DINP |
| 5 | 1 | 1 | OK flex~DINP |
| 6 | 1[b] | 1[b] | Stiff/mod. stiff; flex~or sl. < DINP |
| 7 | 1[c] | 1[c] | Moderately stiff, flex < DINP |
| 8 | 1[c] | 1[c] | OK flex,~or sl. > DINP |
| DINP ctrl for 1-5 | 1 | 1 | OK flex |
| DINP ctrl for 6 | 1[b] | 1[b] | OK flex/sl. stiff |
| DINP ctrl for 7-8 | 1[c] | 1[c] | OK flex/sl. stiff |

*1-5 scale, 1 = no distortion, 5 = completely opaque. No bars exhibited oiliness, stickiness, or inhomogeneity unless otherwise noted.
[a]Evaluated 3 days after pressing.
[b]Evaluated 7 and 39 days after pressing.
[c]Evaluated 13 and 41 days after pressing.

Example 11

98° C. Weight Loss Comparison of PVC Bars Plasticized with Esters Versus PVC Bars Plasticized with Commercial Plasticizer Two each of the PVC sample bars were placed in aluminum weighing pans and placed inside a convection oven at 98° C. Initial weight measurements of the hot bars and measurements taken at specified time intervals were recorded and results were averaged between the bars. The averaged results are shown in Table 5 along with notes on the appearance and flexibility of the bars at the end of the test.

TABLE 5

98° C. % Weight Loss of Ester-Containing PVC Bars and DINP-Containing PVC Control Bars.

| Example No. (Plasticizer Used in Bar) | Day 1 | Day 2 | Day 3 | Day 7 | Day 14 | Day 21 | Notes on Bar* |
|---|---|---|---|---|---|---|---|
| 1 | 0.89 | — | — | 1.17 | — | 8.23 | Very stiff, lt. orange, curled |
| 2 | 0.38 | — | — | 0.81 | — | 4.23 | Stiff, lt. orange, curled |
| 3 | 0.58 | — | — | 2.78 | — | 5.61 | Stiff, lt. orange, curled |
| 4 | 0.57 | — | — | 4.10 | — | 7.79 | Very stiff, lt. orange, curled |
| 5 | 0.42 | — | — | 1.21 | — | 4.10 | Stiff, lt. orange, curled |
| 6 | — | — | 0.52[a] | — | 1.76 | 2.11 | Med. orange, sl, curled, stiff |
| 7 | — | — | 0.29 | 0.44 | 0.72 | 0.89 | Lt. orange, OK flex/sl. stiff |
| 8 | — | — | 0.32 | 0.64 | 1.27 | 1.84 | Lt. orange, sl. curled, OK flex/sl. stiff |
| DINP ctrl for 1-5 | 0.89 | — | — | 0.30 | — | 0.62 | Lt. orange, stiff, sl. curled |
| DINP ctrl for 6 | — | — | 0.39[a] | — | 0.44 | 0.66 | Lt. orange, sl. curled, OK flex/sl. stiff |
| DINP ctrl for 7-8 | — | — | 0.24 | 0.29 | 0.40 | 0.46 | Lt. orange, OK/good flex |

*No bars exhibited oiliness, stickiness, or inhomogeneity unless otherwise noted.
[a]Day 4.

Example 12

70° C. Humid Aging Clarity Comparison of PVC Bars Plasticized with Esters Versus PVC Bars Plasticized with Commercial Plasticizer Using a standard one-hole office paper hole punch, holes were punched in two each of the sample bars ⅛" from one end of the bar. The bars were hung in a glass pint jar (2 bars per jar) containing ~½" of distilled water, sealed, and maintained in a 70° C. convection oven for 21 days. The bars were subsequently equilibrated back to ambient conditions for ~2-4 weeks (until reversible humidity-induced opacity had disappeared). The bars were evaluated visually for clarity. All bars exhibited complete opacity during the duration of the test and for several days after removal from the oven. Results are shown in Table 6 along with notes at the end of the test.

TABLE 6

70° C. Humid Aging Clarity and Appearance Properties of Ester-Containing PVC Bars and DINP-Containing PVC Control Bars.

| Example No. (Plasticizer Used in Bar) | Clarity Value After Test (aged 30 days at ambient)* | Notes on Bar* |
|---|---|---|
| 1 | 1.5 | Very good flex, very minor oil/white spots/haze |
| 2 | 3 | Stiff/somewhat stiff, very oily, curled, hazy |
| 3 | 2.5 | OK flex/sl. stiff, oily, curled, hazy |
| 4 | 3 | Very oily, hazy, sl. stiff |
| 5 | 2 | Good/OK flex, white spots, oil, haze |
| 6 | 1.5 to 2[a] | Stiff, white spots/oil |
| 7 | 1.5[b] | OK flex/sl. stiff |
| 8 | 1[b] | Curled, good flex |
| DINP ctrl for 1-5 | 1 | OK flex, very minor oil/white spots/haze |
| DINP ctrl for 6 | 1[a] | Stiff, minor white spots/oil |
| DINP ctrl for 7-8 | 1[b] | OK flex |

*1-5 scale, 1 = no distortion, 5 = completely opaque. Minor (not major) oil/haze/spots are likely due to very slow (incomplete) equilibration to lose adsorbed water.
[a]Aged for 18 days.
[b]Aged for 20 days.

The data show that effective non-phthalate plasticizers can be made from (alkyl) naphthalene feedstocks using appropriate chemistry, oxidation, optional hydrogenation and selected alcohol or acid chain lengths.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this disclosure and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

The disclosure has been described above with reference to numerous embodiments and specific examples. Many variations will suggest themselves to those skilled in this art in light of the above detailed description. All such obvious variations are within the full intended scope of the appended claims.

What is claimed is:

1. A compound of the formula:

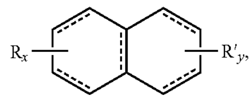

wherein x=8, each R is H, y=4, three of R' are H and one of R' is —OC(O)$R_1$, wherein $R_1$ is a branched $C_4$ to $C_{14}$ alkyl.

2. A compound of the formula:

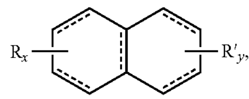

wherein x 4, each R is H, y=4, and R' is H, $C_4$ alkyl, or —OC(O)$R_1$, wherein one of R' is C4 alkyl and at least one of R' is —OC(O)$R_1$, wherein $R_1$ is a branched $C_4$ to $C_{14}$ alkyl.

3. A compound of the formula:

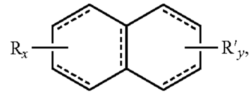

wherein x=8, at least one R is $C_1$ to $C_4$ alkyl, each remaining R is H, y=4, three of R' are H, and one R' is —C(O)O$R_1$ or —OC(O)$R_1$, wherein $R_1$ is a branched $C_4$ to $C_{14}$ alkyl.

4. The compound of claim 1, which are represented by the formula:

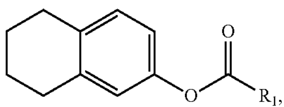

and positional isomers thereof, wherein the one —OC(O) R1 substituent occupies one of the three other sites on the aromatic ring permitted for R'y.

5. A compound represented by the formula:

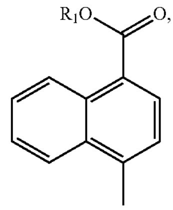

wherein $R_1$ is a branched $C_4$ to $C_{14}$ alkyl, and positional isomers thereof.

6. A compound represented by the formula:

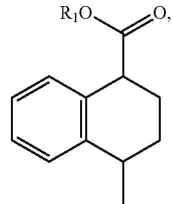

wherein x=8, R is H, $C_1$ to $C_4$ alkyl, —C(O)O$R_1$ or —OC(O)$R_1$, and $R_1$ is a branched $C_4$ to $C_{14}$ alkyl, and positional isomers thereof.

* * * * *